(12) United States Patent
Morgan et al.

(10) Patent No.: US 9,693,884 B1
(45) Date of Patent: Jul. 4, 2017

(54) QUICK RELEASE PROSTHETIC CONNECTOR

(71) Applicant: Sergius Industries LLC, Medford, OR (US)

(72) Inventors: Jedidiah D. Morgan, Medford, OR (US); Stephen E. Harris, Colorado Springs, CO (US)

(73) Assignee: SERGIUS INDUSTRIES, LLC, Medford, OR (US)

(*) Notice: Subject to any disclaimer, the term of this patent is extended or adjusted under 35 U.S.C. 154(b) by 0 days.

(21) Appl. No.: 15/140,421

(22) Filed: Apr. 27, 2016

Related U.S. Application Data

(60) Provisional application No. 62/233,603, filed on Sep. 28, 2015.

(51) Int. Cl.
*A61F 2/78* (2006.01)
*A61F 2/30* (2006.01)

(52) U.S. Cl.
CPC .......... *A61F 2/78* (2013.01); *A61F 2002/305* (2013.01); *A61F 2002/30479* (2013.01); *A61F 2002/30505* (2013.01); *A61F 2220/0008* (2013.01)

(58) Field of Classification Search
CPC .. A61F 2002/30479; A61F 2002/30505; A61F 2002/7875; A61F 2220/00; A61F 2220/0008; A61F 2220/0033; A61F 2/78
See application file for complete search history.

(56) References Cited

U.S. PATENT DOCUMENTS 5,226,918 A 7/1993 Silagy et al.
6,432,110 B1 8/2002 Richelsoph
(Continued)

*Primary Examiner* — Bruce E Snow
(74) *Attorney, Agent, or Firm* — Jerry Haynes Law

(57) ABSTRACT

A quick release prosthetic connector for detachably joining a threaded prosthetic socket to a prosthetic includes a socket-connect portion configured for connection to the prosthetic socket. A plurality of locking members is carried by the socket-connect portion. The plurality of locking members are positional between a release position and a locking position and normally biased in the locking position. A prosthetic-connect portion is configured for connection to the prosthetic. A plurality of locking member engaging apertures is provided in the prosthetic-connect portion. The plurality of locking member engaging apertures are configured to selectively receive the plurality of locking members, respectively, of the socket-connect portion in the locking position of the plurality of locking members. A lock portion is carried by the socket-connect portion. The lock portion is configured to selectively lock and release the prosthetic-connect portion with respect to the socket-connect portion. A plurality of lock portion depressions is provided in the lock portion. The plurality of lock portion depressions is configured to selectively receive the plurality of locking members, respectively, of the socket-connect portion in the locking position of the plurality of locking members. The plurality of locking members are deployed in the locking position and extend through the plurality of locking member engaging apertures, respectively, in the prosthetic-connect portion and seat in the respective lock portion depressions in the lock portion responsive to rotation of the lock portion in a first direction. The plurality of locking members are deployed in the unlocking position and disengage the plurality of locking member engaging apertures, respectively, in the prosthetic-connect portion and the respective lock portion depressions in the lock portion responsive to rotation of the lock portion in a second direction.

18 Claims, 16 Drawing Sheets

(56) References Cited

U.S. PATENT DOCUMENTS

| | | | |
|---|---|---|---|
| 6,440,173 | B1 | 8/2002 | Meyer |
| 6,589,289 | B2 | 7/2003 | Ingimarsson |
| 7,048,768 | B1 | 5/2006 | Rouse et al. |
| 7,288,117 | B2 | 10/2007 | Benson |
| 8,512,416 | B2 | 8/2013 | Porter et al. |
| 9,028,560 | B2 * | 5/2015 | Farquharson ............ A61F 2/54 |
| | | | 623/57 |
| 9,089,444 | B2 | 7/2015 | Soss et al. |
| 2007/0021841 | A1 | 1/2007 | Al-Temen et al. |
| 2009/0292368 | A1 | 11/2009 | Plowman |
| 2013/0337724 | A1 | 12/2013 | Porter et al. |
| 2014/0188252 | A1 | 7/2014 | Sadler et al. |
| 2014/0358248 | A1 | 12/2014 | Will et al. |

\* cited by examiner

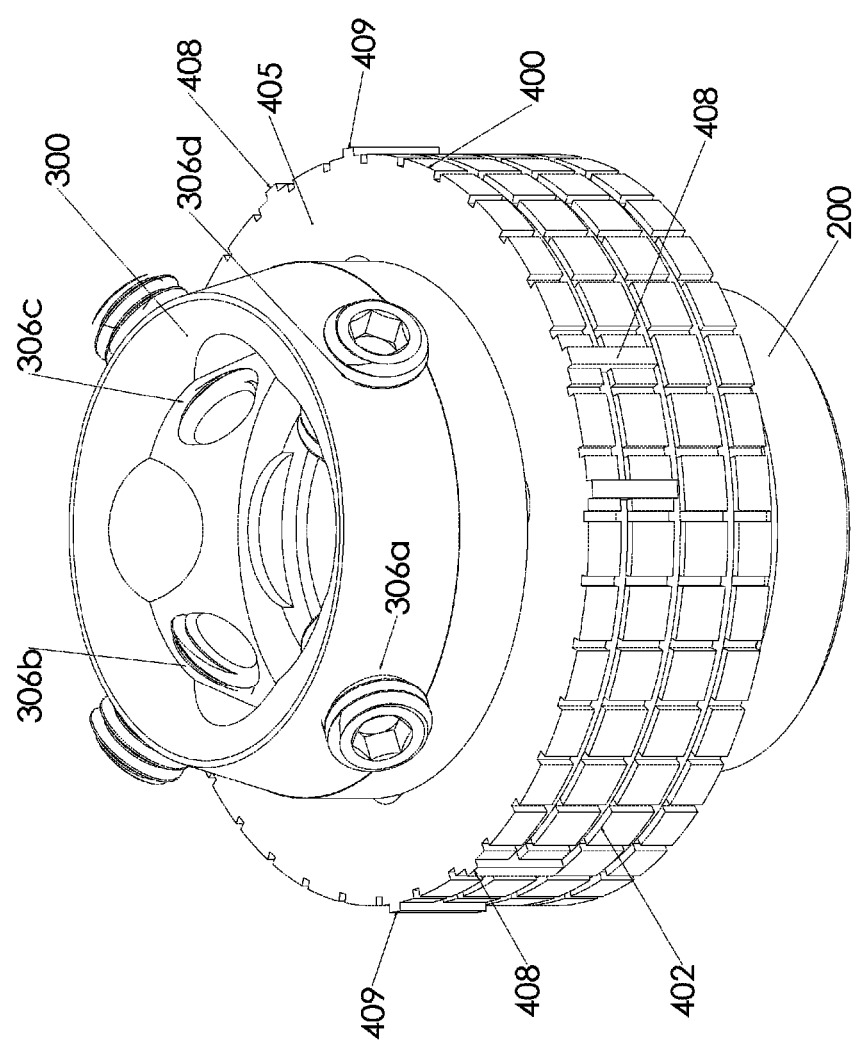

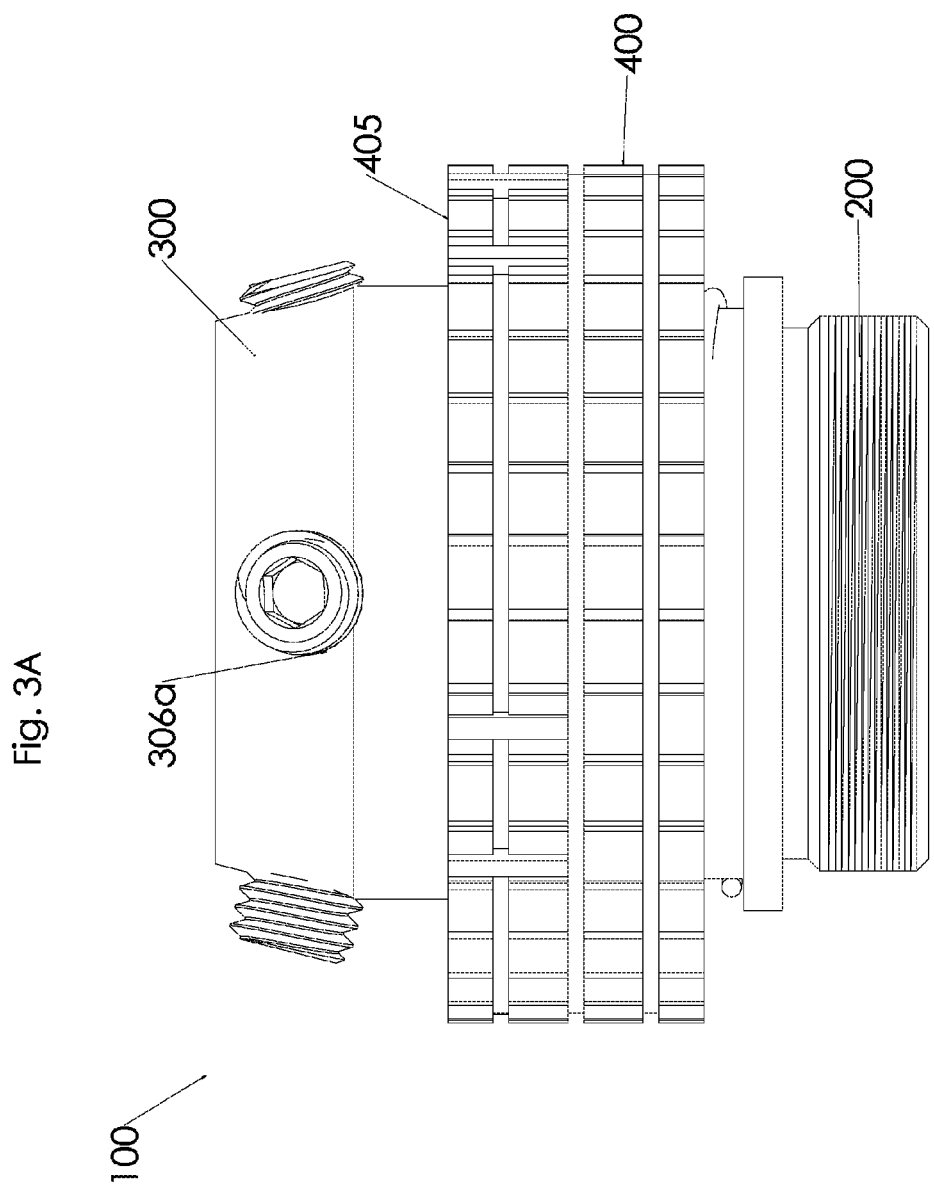

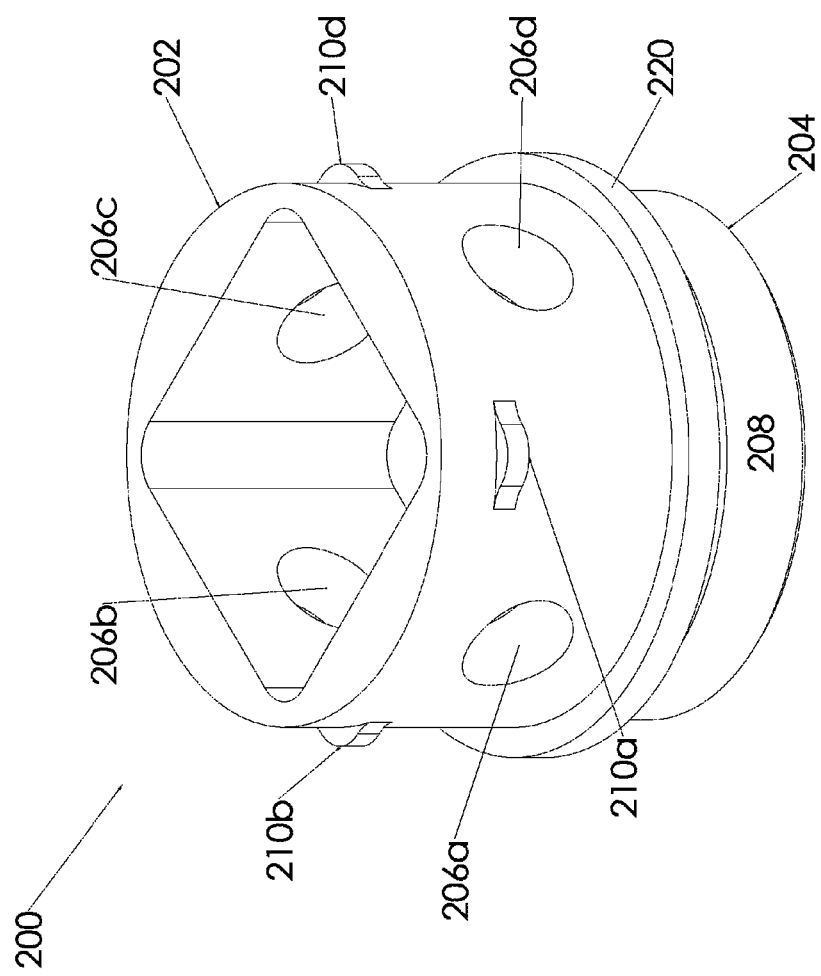

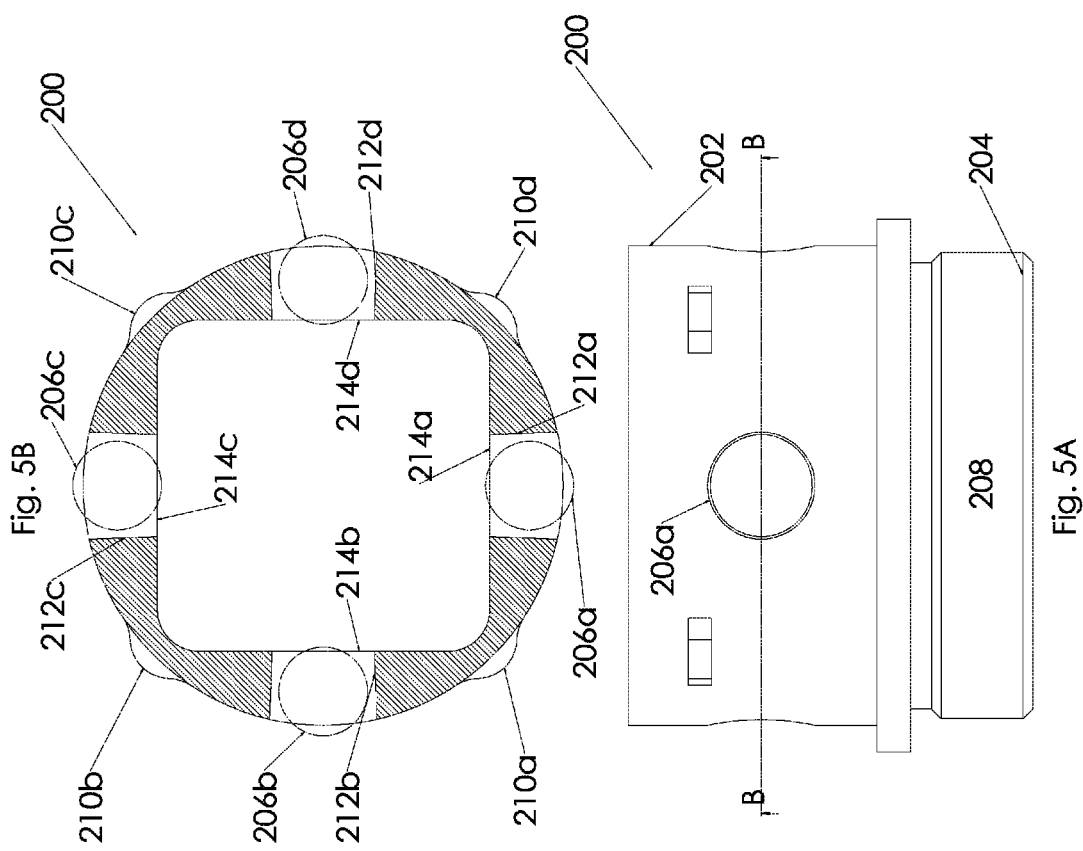

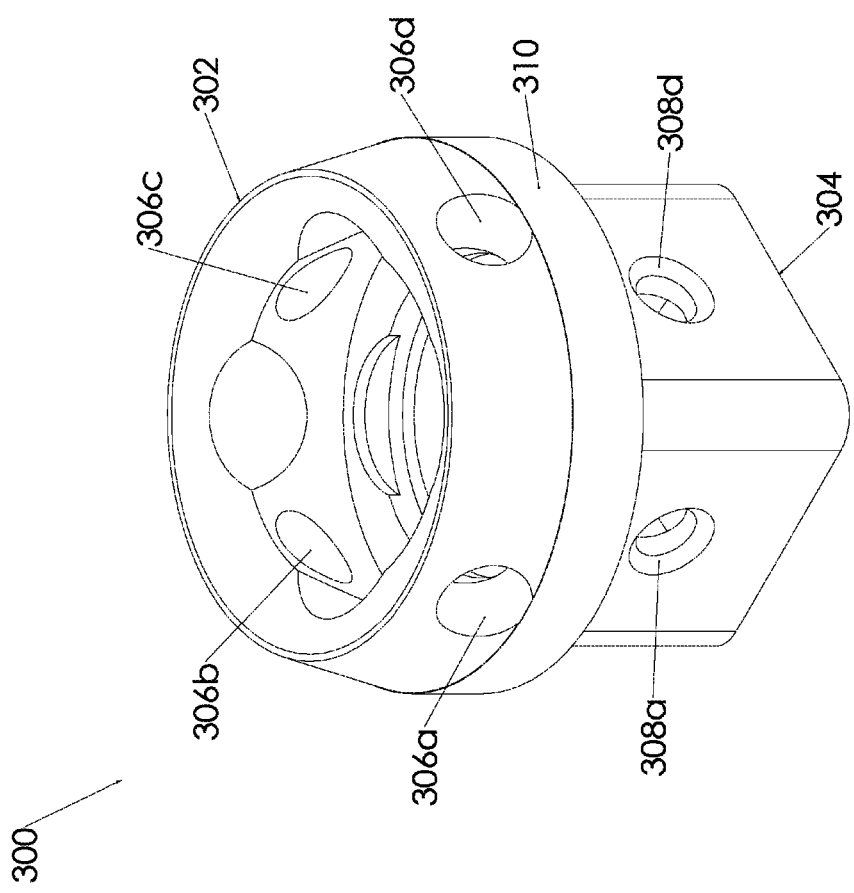

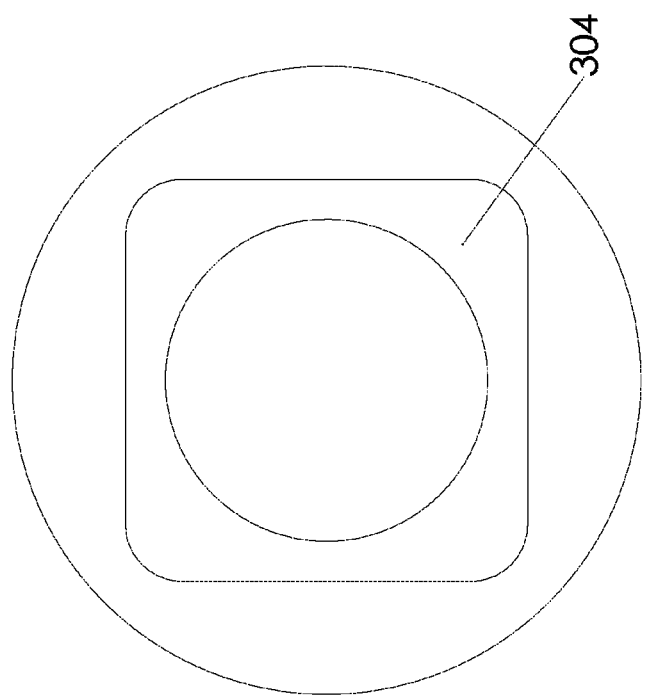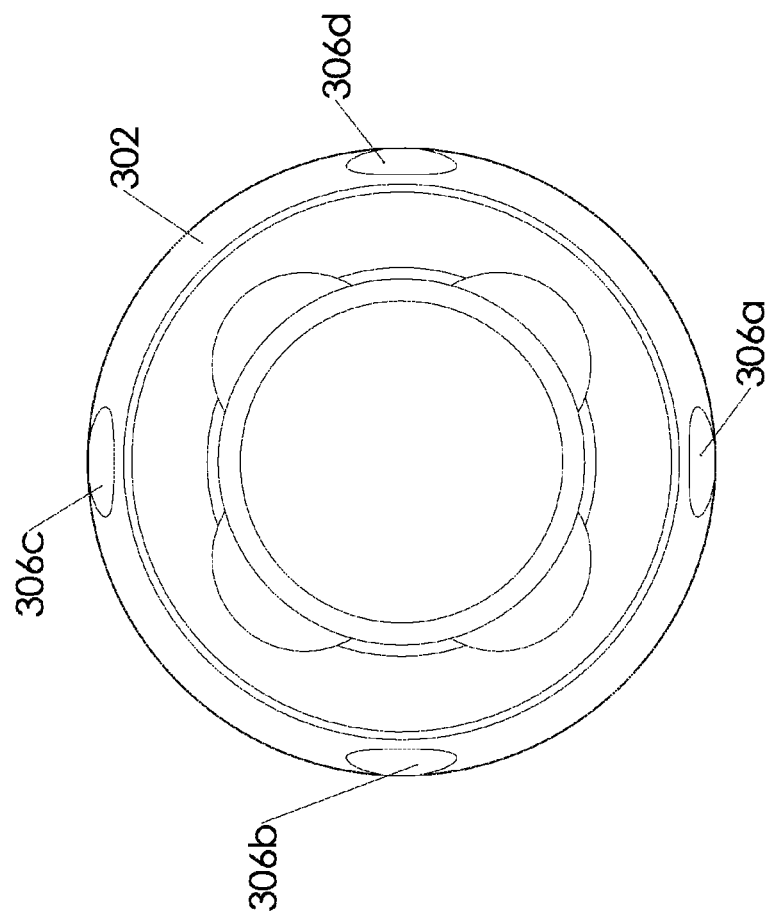

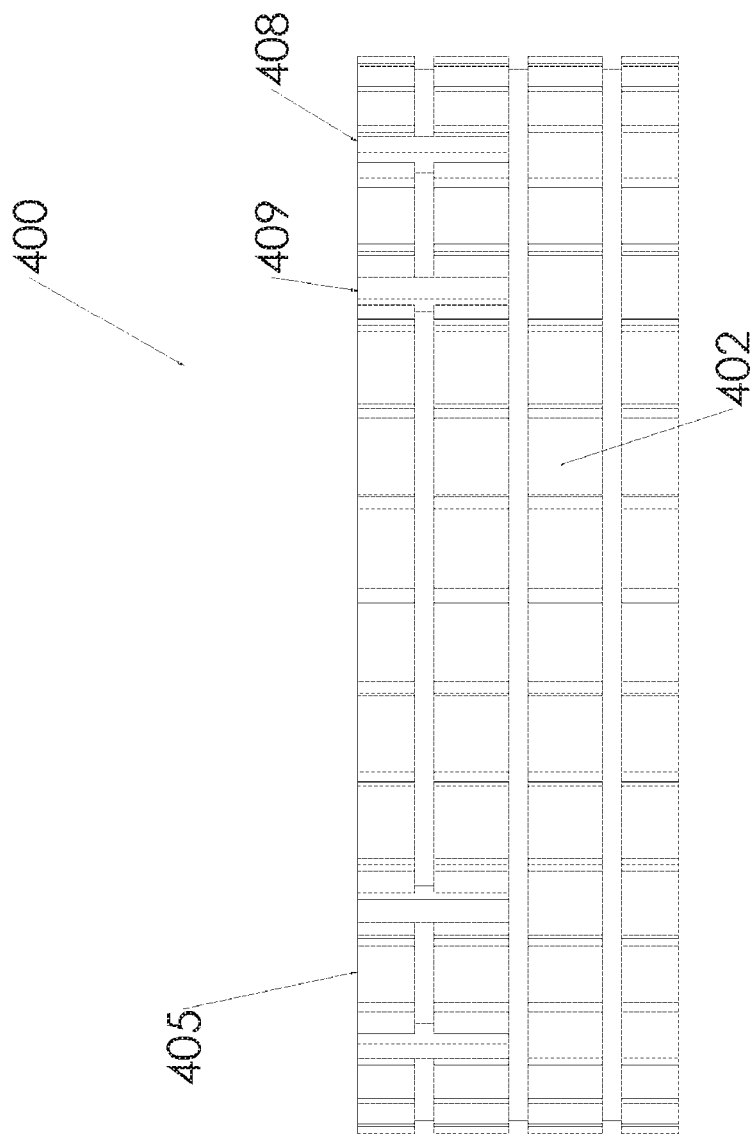

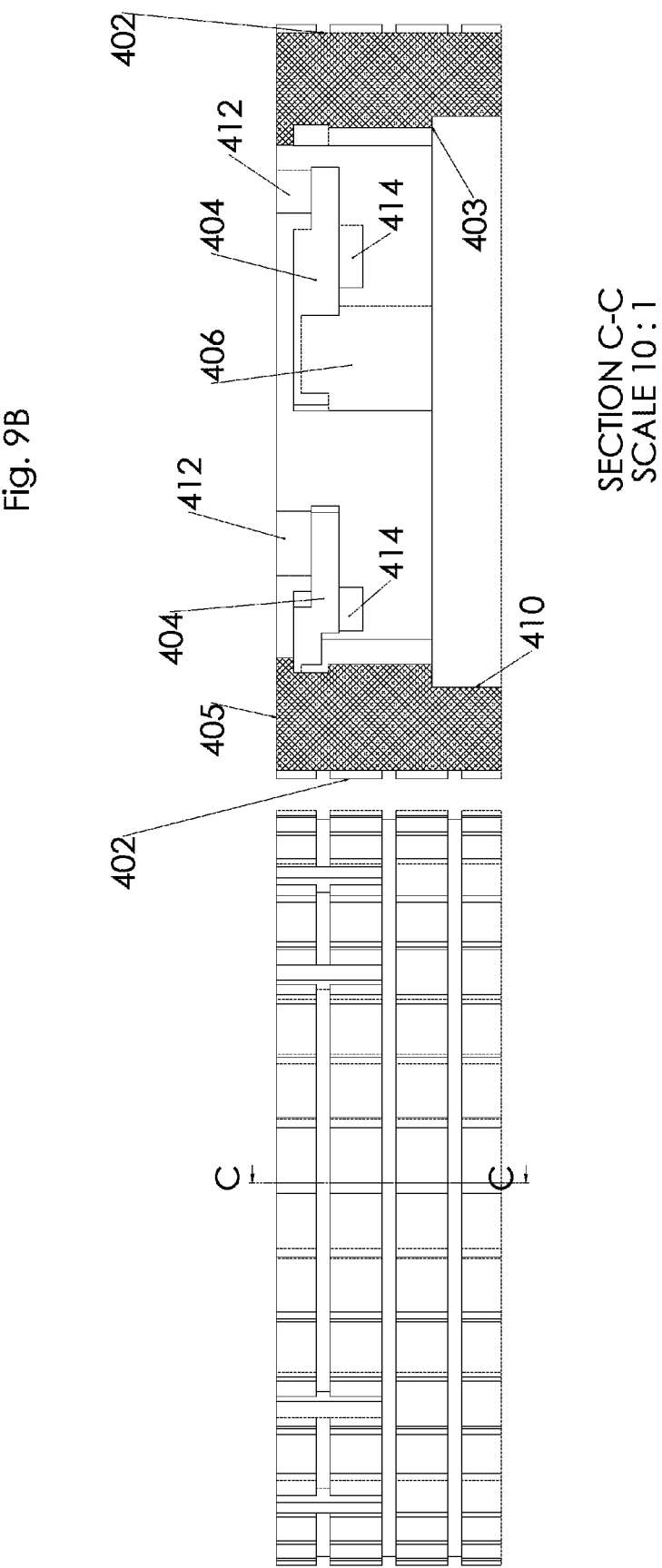

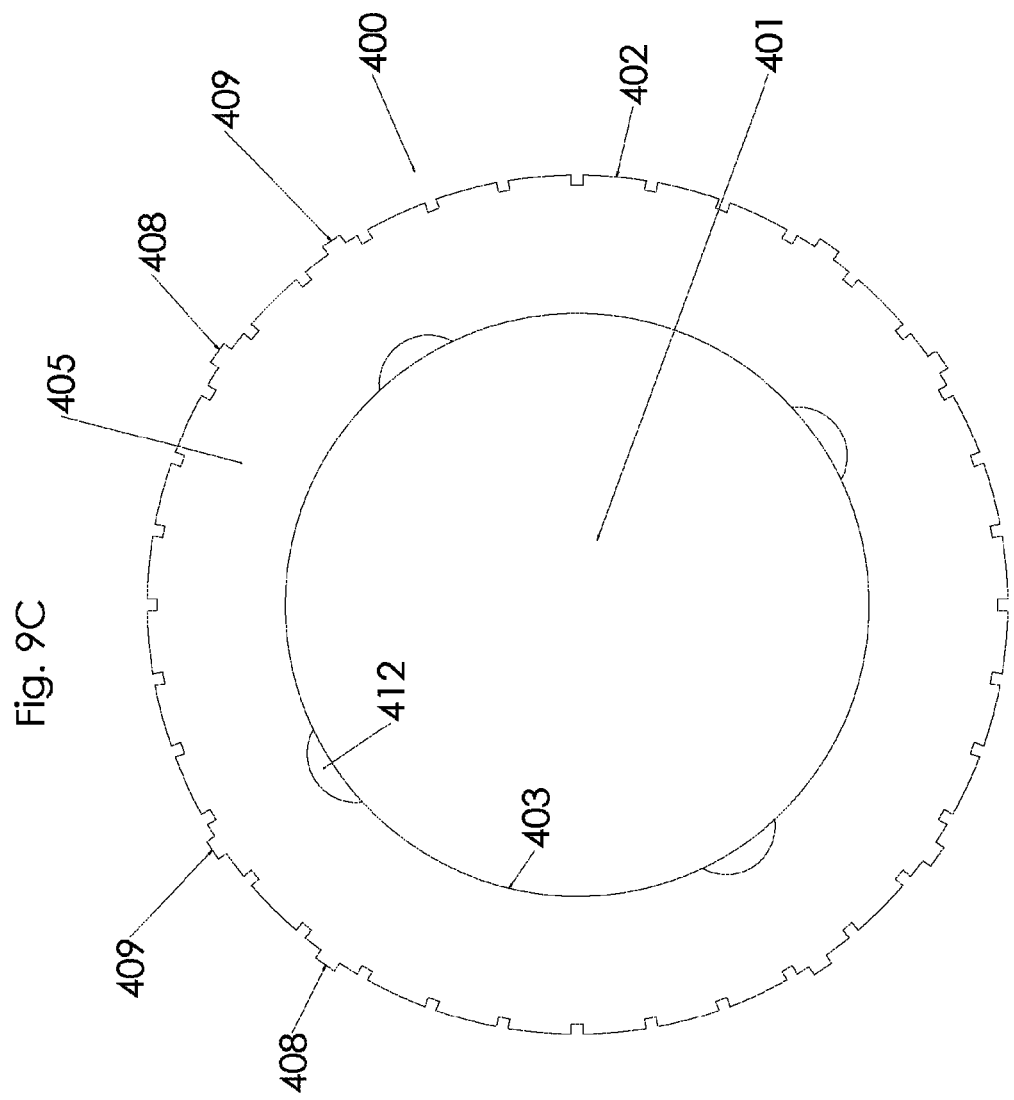

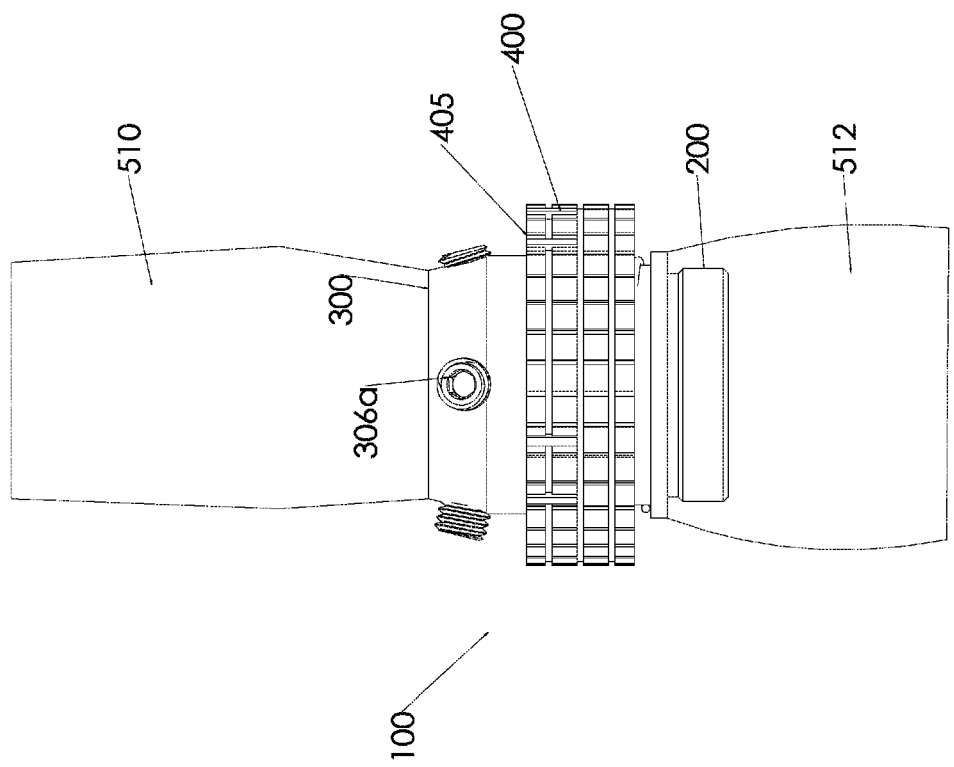

QUICK RELEASE PROSTHETIC CONNECTOR

CROSS-REFERENCE TO RELATED APPLICATIONS

This application claims the benefit of U.S. provisional application No. 62/233,603, filed Sep. 28, 2015 and entitled QUICK RELEASE PROSTHETIC CONNECTOR, which application is incorporated by reference herein in its entirety.

FIELD OF THE INVENTION

The present invention relates generally to a quick release prosthetic connector that detachably attaches a prosthetic to a prosthetic socket. More so, the present invention relates to a quick release prosthetic connector that detachably attaches a prosthetic to a prosthetic socket and includes a socket-connect portion having a plurality of locking members, a plurality of spring members biasing the plurality of locking members, at least one protrusion, a threaded outer surface, and a typically threaded inner surface that detachably couples to a threaded prosthetic socket; a prosthetic-connect portion having a plurality of prosthetic apertures that enable passage of at least one fastener for fastening to a prosthetic, and a plurality of locking member engaging apertures that selectively receive the respective locking members of the socket-connect portion; and a lock portion having a threaded locking surface configured to rotatably fasten to the threaded outer surface of the socket-connect portion, a plurality of lock portion depressions that selectively receive the respective locking members of the socket-connect portion, and at least one lock portion channel having a lock notch and a release notch that selectively align with the at least one protrusion of the socket-connect portion; whereby alignment of the lock notch with the at least one protrusion extends the locking members into the respective lock portion depressions, locking the prosthetic-connect portion to the socket-connect portion; and whereby alignment of the release notch with the at least one protrusion disengages the locking members from the respective lock portion depressions, facilitating release and detachment of the prosthetic-connect portion from the socket-connect portion.

BRIEF DESCRIPTION OF THE DRAWINGS

The invention will now be described, by way of example, with reference to the accompanying drawings, in which:

FIG. 2 illustrates a perspective view of a quick release prosthetic connector dissembled into an exemplary prosthetic-connect portion, an exemplary socket-connect portion, and an exemplary lock portion, in accordance with an embodiment of the present invention;

FIG. 3A illustrates a side view of a quick release prosthetic connector in accordance with an embodiment of the present invention;

FIG. 4 illustrates a top angle perspective view of an exemplary socket-connect portion of the quick release prosthetic connector in accordance with an embodiment of the present invention;

FIG. 5A illustrates a side view of an exemplary socket-connect portion of the quick release prosthetic connector in accordance with an embodiment of the present invention;

FIG. 5B illustrates a cross-sectional view, taken along section lines 5B-5B in FIG. 5A, of the exemplary socket-connect portion of the quick release prosthetic connector in accordance with an embodiment of the present invention;

FIG. 6 illustrates a top angle perspective view of an exemplary prosthetic-connect portion of the quick release prosthetic connector, in accordance with an embodiment of the present invention;

FIG. 7C illustrates a top view of the exemplary prosthetic-connect portion of the quick-release prosthetic connector, in accordance with an embodiment of the present invention;

FIG. 7D illustrates a bottom view of the exemplary prosthetic-connect portion of the quick-release prosthetic connector, in accordance with an embodiment of the present invention;

FIG. 9A illustrates a side view of the exemplary lock portion of the quick-release prosthetic connector, in accordance with an embodiment of the present invention;

FIG. 9B illustrates a cross-sectional view of the exemplary lock portion of the quick-release prosthetic connector, detailing a channel and a plurality of depressions in the lock portion, in accordance with an embodiment of the present invention;

FIG. 9C illustrates a top view of the exemplary lock portion of the quick-release prosthetic connector, in accordance with an embodiment of the present invention;

FIG. 10 illustrates a side view of a quick release prosthetic connector in accordance with an embodiment of the present invention, coupling a prosthetic to a prosthetic socket in typical application of the connector.

Like reference numerals refer to like parts throughout the various views of the drawings.

DETAILED DESCRIPTION OF THE INVENTION

The following detailed description is merely exemplary in nature and is not intended to limit the described embodiments or the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to make or use the embodiments of the disclosure and are not intended to limit the scope of the disclosure, which is defined by the claims. For purposes of description herein, the terms "upper," "lower," "left," "rear," "right," "front," "vertical," "horizontal," and derivatives thereof shall relate to the invention as oriented in FIG. 1. Furthermore, there is no intention to be bound by any expressed or implied theory presented in the preceding technical field, background, brief summary or the following detailed description. It is also to be understood that the specific devices and processes illustrated in the attached drawings, and described in the following specification, are simply exemplary embodiments of the inventive concepts defined in the appended claims. Specific dimensions and other physical characteristics relating to the embodiments disclosed herein are therefore not to be considered as limiting, unless the claims expressly state otherwise.

Referring initially to FIGS. 1, 2, 3A, 3B, and 10 of the drawings, an exemplary embodiment of a quick release prosthetic connector 100 is illustrated. As illustrated in FIG. 10 and will be hereinafter further described, in typical application, the quick release prosthetic connector 100 detachably attaches or couples a prosthetic socket 512 to a prosthetic 510. The quick release prosthetic connector 100, hereafter, "connector 100", may utilize threaded surfaces and tensioned friction fit locking mechanisms to enable quick attachment and release of the prosthetic 510 with respect to the prosthetic socket 512, as will be hereinafter described.

The quick release functionality of the connector 100 may enable the prosthetic 510 to be removed from the prosthetic socket 512 without the necessity of performing the laborious steps of removing the entire prosthetic socket 512 from a residual limb (not illustrated) to which it is attached, as is presently required by the prior art. Also, the quick release functionality of the connector 100 may enable one-handed detachable attachment of the prosthetic 510 to the prosthetic socket 512. In this manner, greater flexibility and maneuverability may be allowed for a prosthetic wearer in attachment and detachment of the prosthetic 510 with respect to the residual limb.

Figure 1:
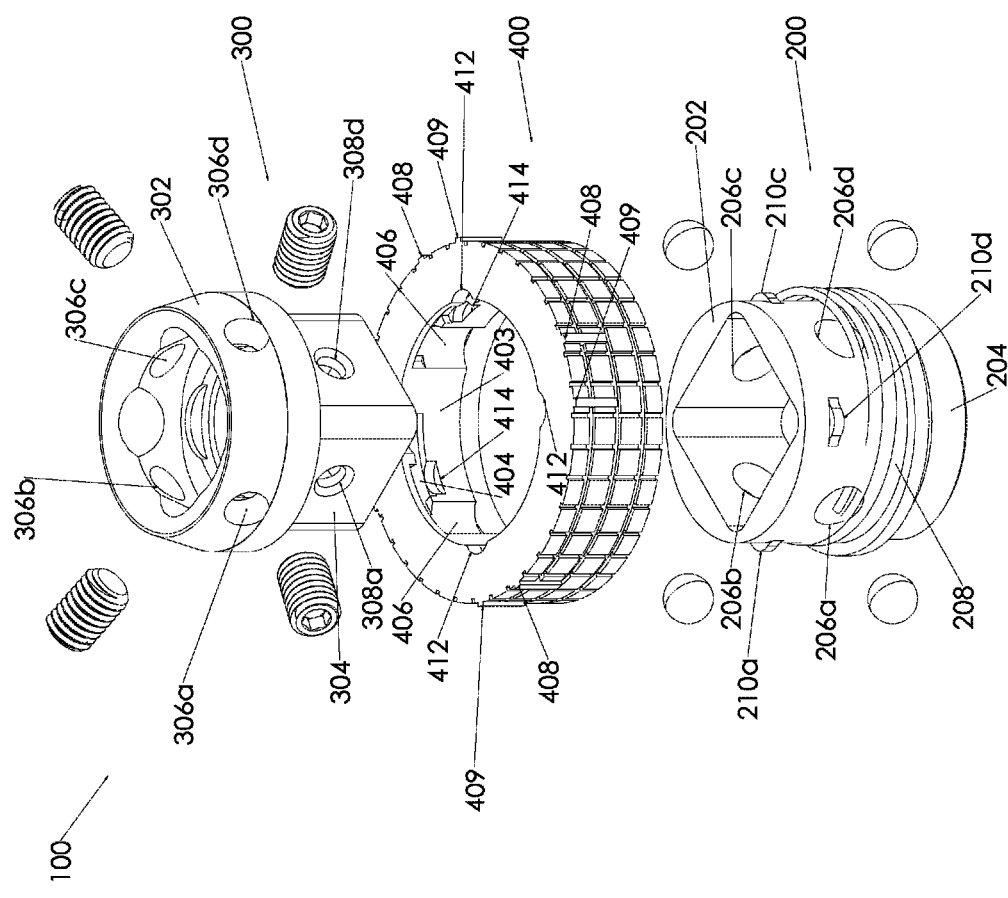
FIG. 1 illustrates an exploded perspective top angle view of an exemplary quick release prosthetic connector fully assembled, in accordance with an embodiment of the present invention.
Figure 3B:
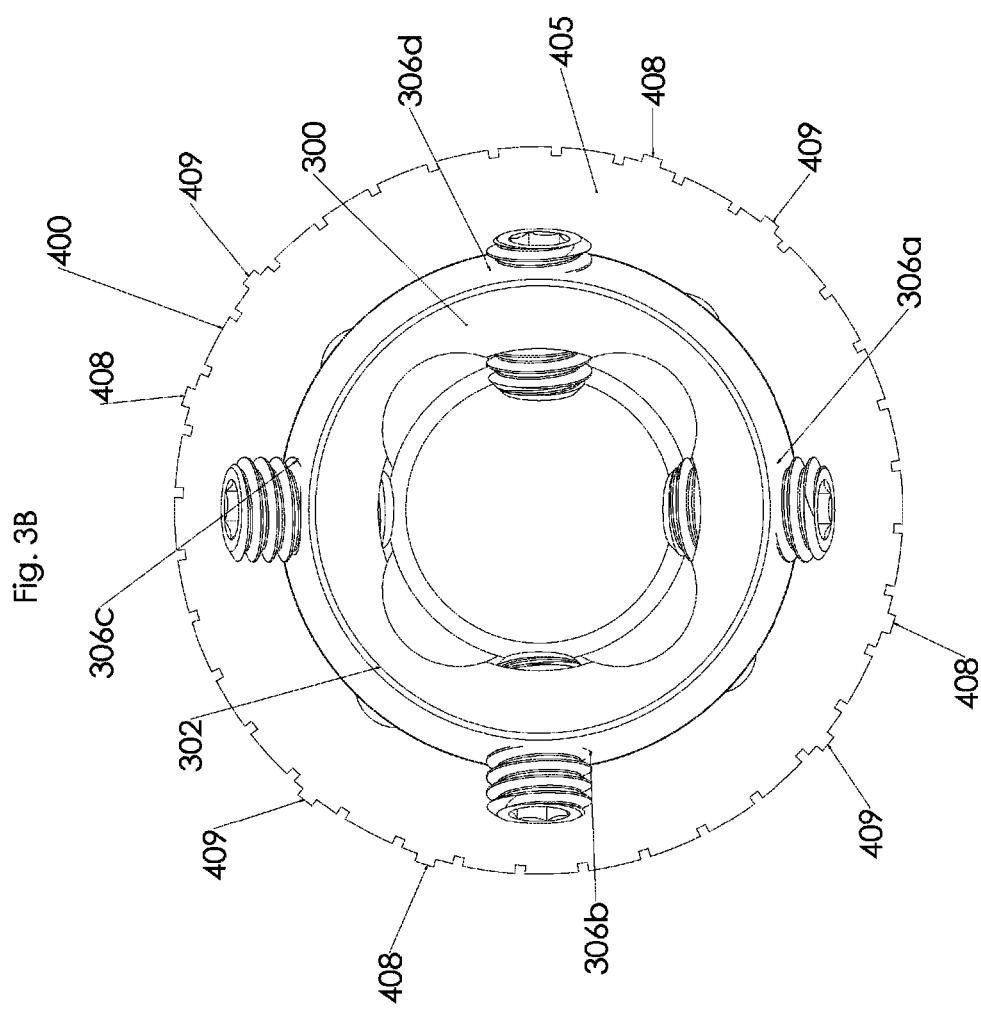
FIG. 3B illustrates a top view of a quick release prosthetic connector in accordance with an embodiment of the present invention.

In typical application, the connector 100 may detachably join a threaded prosthetic socket 512 to a prosthetic 510. As illustrated in FIG. 1, the connector 100 may include a socket-connect portion 200 which attaches to the prosthetic socket 512 (FIG. 10), a prosthetic-connect portion 300 which attaches to the prosthetic 510 and a lock portion 400 that detachably couples the prosthetic-connect portion 300 to the socket-connect portion 200 to form a quick release interface between the prosthetic 510 and the prosthetic socket 512. In some embodiments, the socket-connect portion 200 may detachably attach to the prosthetic socket 512. This detachable attachment of the socket-connect portion 200 to the prosthetic socket 512 may be achieved through rotational engagement between threaded surfaces on the respective socket-connect portion 200 and the prosthetic socket 512, for example and without limitation.

The prosthetic 510 may detachably attach to the prosthetic-connect portion 300. In some embodiments, this detachable attachment between the prosthetic 510 and the prosthetic-connect portion 300 may be achieved through a fixed connection involving at least one fastener (not illustrated) that passes through at least one prosthetic aperture 306a-d in the prosthetic-connect portion 300 and into a registering fastener aperture (not illustrated) in the prosthetic 510, for example and without limitation.

The lock portion 400 may detachably fasten the prosthetic-connect portion 300 to the socket-connect portion 200. The lock portion 400 may additionally control a lock and release mechanism that enables quick release of the prosthetic 510 from the prosthetic socket 512. In some embodiments, the lock portion 400 may utilize threaded surfaces and typically spherical friction-fit locking members 206a-d to selectively lock and release the prosthetic 510 with respect to the prosthetic socket 512, as will be hereinafter described.

Those skilled in the art will recognize that a prosthetic socket 512 is designed to act as an interface between a residual limb and a prosthetic 510. The primary function of the prosthetic socket 512 is to contain and protect the residual limb and transfer forces from the residual limb to the prosthetic 510 throughout the normal daily activities of the prosthetic wearer. In some embodiments, the connector 100 may be operable with a threaded prosthetic socket 512. The connector 100 may be applicable to any type of prosthetic 510, including, without limitation, a foot, a hand, a leg, an arm, and a tail.

As further illustrated in FIG. 1, in some embodiments, the quick release prosthetic connector 100 for detachably joining a prosthetic socket 512 (FIG. 10) to a prosthetic 510 may include:

a socket-connect portion 200, the socket-connect portion 200 defined by a generally elongated tubular shape having a broad socket-connect portion end 202 and a narrow socket-connect portion end 204, the broad socket-connect portion end 202 including a plurality of locking member openings 212a-d (FIG. 5B), a plurality of typically spherical locking members 206a-d disposed in the respective locking member openings 212a-d, a plurality of spring members 214a-d (FIG. 5B) engaging the respective locking members 206a-206d, a threaded socket-connect portion outer surface 208, and at least one protrusion 210a-d extending from the broad socket-connect portion end 202, the narrow socket-connect portion end 204 having a threaded socket-connect portion inner surface 216 (FIG. 5D), whereby the plurality of spring members 214a-214d are configured to normally bias and protrude the plurality of locking members 206a-d outwardly from the respective locking member openings 212a-d beyond the threaded socket-connect portion outer surface 208 of the socket-connect portion 200, whereby the threaded socket-connect portion inner surface 216 is configured to enable detachable coupling of the socket-connect portion 200 to a prosthetic socket 512 (FIG. 10);

a prosthetic-connect portion 300, the prosthetic-connect portion 300 defined by a generally elongated shape and having a prosthetic-connect portion head end 302 and a prosthetic-connect portion base end 304, the prosthetic-connect portion head end 302 comprising at least one prosthetic aperture 306a-d configured to accommodate passage of a corresponding at least one fastener (not illustrated) for fastening the prosthetic 510 to the prosthetic-connect portion 300, the prosthetic-connect portion base end 304 comprising a plurality of typically spherical locking member engaging apertures 308a-d configured to selectively receive the plurality of locking members 206a-d, respectively, of the socket-connect portion 200;

a lock portion 400, the lock portion 400 configured to selectively lock and release the prosthetic-connect portion 300 with respect to the socket-connect portion 200, the lock portion 400 defined by a generally annular shape, the lock portion 400 having a lock portion opening 401, a lock portion end surface 405 facing the prosthetic-connect portion 300, an interior lock portion surface 403 facing the lock portion opening 401, lock portion threads 410 in the interior lock portion surface 403 to rotatably engage the threaded socket-connect portion outer surface 208 of the socket-connect portion 200, an exterior lock portion surface 402, the lock portion 400 further having at least one lock portion channel 404 in the interior lock portion surface 403 and configured to selectively align and mate with the corresponding at least one protrusion 210a-d of the socket-connect portion 200 and a release notch 412 and a lock notch 414 communicating with the at least one lock portion channel 404 in offset relationship to each other, the lock portion 400 further having a plurality of lock portion depressions 406 in the interior lock portion surface 403 and configured to selectively receive the plurality of locking members 206a-d, respectively, of the socket-connect portion 200;

whereby alignment of the at least one protrusion 210a-d on the socket-connect portion 200 with the at least one lock notch 414 in the interior lock portion surface 403 of the lock portion 400 facilitates extension of the plurality of locking members 206a-d through the plurality of locking member engaging apertures 308a-d in the prosthetic-connect portion 300 and into the plurality of lock portion depressions 406 in the lock portion 400, locking the prosthetic-connect portion 300 with respect to the socket-connect portion 200, whereby alignment of the at least one protrusion 210a-d with the at least one release notch 412 causes the plurality of locking members 206a-d to disengage the plurality of lock portion depressions 406, facilitating release of the prosthetic-connect portion 300 from the socket-connect portion 200, whereby rotational and axial forces applied to the lock portion 400 facilitate traversal of the at least one protrusion 210a-d along the at least one lock portion channel 404 and selective positioning of the at least one protrusion 210a-d in the at least one release notch 412 or the at least one lock notch 414;

at least one lock portion slit 408 in at least one of the exterior lock portion surface 402 and the lock portion end surface 405 of the lock portion 400, the at least one lock portion slit 408 disposed adjacently to and in alignment with the lock notch 414, the at least one lock portion slit 408 configured to indicate alignment of the at least one protrusion 210a-d on the socket-connect portion 200 with the lock notch 414 in the lock portion 400; and at least one release portion slit 409 in at least one of the exterior lock portion surface 402 and the lock portion end surface 405 of the lock portion 400, the at least one release portion slit 409 disposed adjacently to and in alignment with the release notch 412, the at least one release portion slit 409 configured to indicate alignment of the at least one protrusion 210a-d on the socket-connect portion 200 with the release notch 412 in the lock portion 400.

In another aspect, the prosthetic 510 may include at least one member selected from the group consisting of: a foot, a hand, a leg, an arm, and a tail.

In another aspect, the prosthetic socket 512 may include a threaded prosthetic socket configured to rotatably engage the threaded socket-connect portion inner surface 216 of the socket-connect portion 200.

In another aspect, the plurality of locking members 206a-d may include four metal balls.

In another aspect, the plurality of spring members 214a-d may include four springs that bias the plurality of locking members 206a-d, respectively, outwardly beyond the threaded socket-connect portion outer surface 208 of the socket-connect portion 200.

In another aspect, the at least one protrusion 210a-d may include at least one tab.

In another aspect, the lock portion 400 may form a ring that encompasses the socket-connect portion 200.

One objective of the present invention is to enable a quick release of the prosthetic-connect portion 300 and the attached prosthetic 510 from the socket-connect portion 200 and the attached prosthetic socket 512.

Another objective is to enable one-handed release and attachment of a prosthetic 510 with respect to a prosthetic socket 512.

Yet another objective is to enable facilitated interchangeable attachment of different prosthetics 510 to a prosthetic socket 512.

Yet another objective is to facilitate temporary detachment of a prosthetic 510 when a prosthetic wearer is entering or leaving a confined space such as a vehicle seat.

Yet another objective is to provide an inexpensive-to-manufacture quick-release prosthetic connector 100.

Referring next to FIGS. 1-10 of the drawings, in some embodiments, the connector 100 may include a socket-connect portion 200, a prosthetic-connect portion 300, and a lock portion 400 that detachably couples the prosthetic-connect portion 300 to the socket-connect portion 200 to form an interface between a prosthetic 510 and a prosthetic socket 512 on a residual limb (not illustrated) of a prosthetic wearer, as illustrated in FIG. 10. Suitable materials for the connector 100 and associated components may include, without limitation, titanium, aluminum, polypropylene, nylon, Dacron™, Kevlar™, and carbon.

FIG. 1 illustrates the socket-connect portion 200, the prosthetic-connect portion 300 and the lock portion 400 of the disassembled connector 100, whereas FIG. 2 illustrates the assembled connector 100. The socket-connect portion 200 of the connector 100 may be configured to detachably attach to the prosthetic socket 512 according to any suitable technique which is known by those skilled in the art. In some embodiments, attachment of the socket-connect portion 200 to the prosthetic socket 512 may be achieved through rotational engagement between threaded surfaces on the respective socket-connect portion 200 and prosthetic socket 512. Other means of attachment which are suitable for the purpose may include screws, magnets, adhesives and/or friction fitting, for example and without limitation. The lock portion 400 may detachably attach the prosthetic-connect portion 300 to the socket-connect portion 200 typically in a manner which will be hereinafter described.

As illustrated in FIG. 10, the prosthetic 510 may be configured for detachable attachment to the prosthetic-connect portion 300 of the connector 100. In some applications, this attachment may be achieved through a fixed connection involving at least one fastener (not illustrated) that passes through a corresponding at least one or a plurality of prosthetic apertures 306a-d typically in the prosthetic-connect head portion end 302 of the prosthetic-connect portion 300. The lock portion 400 may detachably secure the prosthetic-connect portion 300 to the socket-connect portion 200 while also controlling the lock and release mechanism that enables quick release of the prosthetic 512 from the residual limb to which the prosthetic socket 512 is attached. The quick release mechanism may utilize threaded surfaces and tensioned or spring-loaded locking members 206a-d which protrude through respective locking member engaging apertures 308a-d that are typically in the prosthetic-connect base portion end 304 of the prosthetic-connect portion 300 and into and out of engagement with respective lock portion depressions 406 in the interior lock portion surface 403 of the lock portion 400.

As illustrated in FIG. 4, the socket-connect portion 200 may be defined by a generally elongated tubular shape with a broad socket-connect portion end 202 and a narrow socket-connect portion end 204. A circumferential socket ridge 220 may extend from the outer surface of the socket-connect portion 200 between the broad socket-connect portion end 202 and the narrow socket-connect portion end 204. As illustrated in FIG. 5B, in some embodiments, a plurality of spaced-apart locking member openings 212a-d may be provided typically in the broad socket-connection end 202 of the socket-connect portion 200. A plurality of locking members 206a-d, each of which may be spherical, may be provided in the respective locking member openings 212a-d. A plurality of spring members 214a-214d may be provided in the respective locking member openings 212a-d. As further illustrated in FIG. 5B, the spring members 214a-d may normally engage and bias the locking members 206a-d in an extended or protruded configuration from the respective locking member openings 212a-d. As will be hereinafter described, responsive to clockwise or counterclockwise rotation of the lock portion 400, the locking members 206a-d may reversibly insert through the locking member engaging apertures 308a-d in the prosthetic-connect portion 300 and snap or seat into the respective lock portion depressions 406 in the lock portion 400 to selectively lock and release the socket-connect portion 200 with respect to the prosthetic-connect portion 300. In some embodiments, the locking members 206a-d may include four metal balls.

As illustrated in FIGS. 5A and 5B, the narrow socket-connect portion end 204 of the socket-connect portion 200 may further include a threaded socket-connect portion outer surface 208 that threadably engages the companion lock portion threads 410 (FIG. 9B) in the interior lock portion surface 403 of the lock portion 400. The broad socket-connect portion end 202 may include the plurality of spring members 214a-d (FIG. 5B) in the respective locking member openings 212a-d. The spring members 214a-d may be configured to bias and protrude the respective locking members 206a-d from the locking member openings 212a-d beyond the threaded socket-connect portion outer surface 208 and through the locking member engaging apertures 308a-d in the prosthetic-connect portion 300 and into the respective lock portion depressions 406 in the lock portion 400 to detachably lock the prosthetic-connect portion 300 to the socket-connect portion 200.

In some embodiments, the lock portion 400 may be rotated in a first direction to force the locking members 206a-d into the respective locking member openings 212a-d, against the bias imparted by the respective spring members 214a-d, and in a second direction to extend the locking members 206a-d to their respective biased positions in which the spring members 214a-d protrude from the respective locking member openings 212a-d beyond the threaded socket-connect portion outer surface 208. As discussed below, this in-and-out movement of the locking members 206a-d may create a mechanism by which prosthetic-connect portion 300 is selectively locked and released with respect to the socket-connect portion 200. The broad socket-connect portion end 202 may further include at least one protrusion 210a-d for purposes which will be hereinafter described. In some embodiments, the at least one protrusion 210a-d may include four tabs.

Figure 5D:
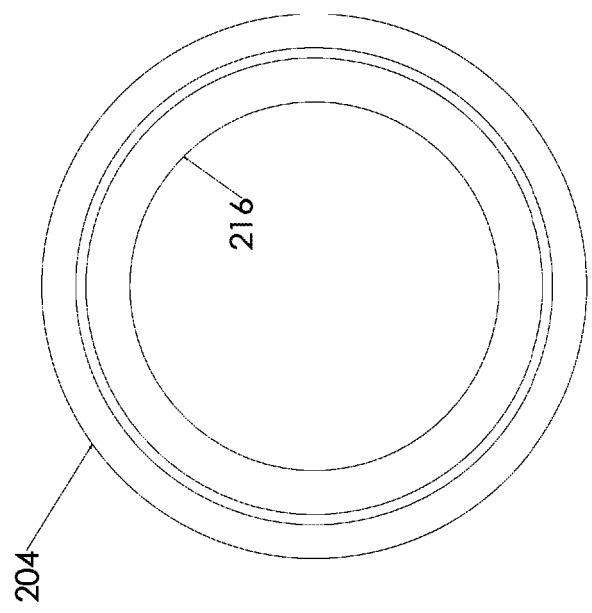
FIG. 5D illustrates a bottom view of the exemplary socket-connect portion of the quick release prosthetic connector in accordance with an embodiment of the present invention.
Figure 5C:
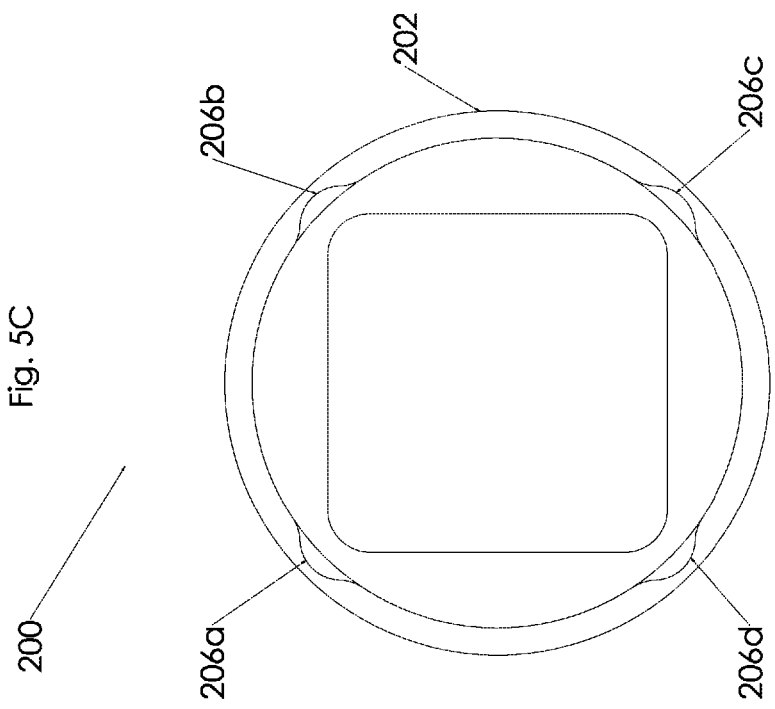
FIG. 5C illustrates a top view of the exemplary socket-connect portion of the quick release prosthetic connector in accordance with an embodiment of the present invention.

As illustrated in FIG. 5D, in some embodiments, the narrow socket-connect portion end 204 of the socket-connect portion 200 may include a threaded socket-connect portion inner surface 216 that rotatably engages the exterior threaded surface (not illustrated) of the prosthetic socket 512 to join the socket-connect portion 200 to the prosthetic socket 512. In other embodiments, the socket-connect portion end 204 may fasten to the prosthetic socket 512 through screws, magnets, adhesives and/or frictional fitting, for example and without limitation.

As illustrated in FIG. 1, the connector 100 may further include a prosthetic-connect portion 300. The prosthetic-connect portion 300 may be configured for attachment to the prosthetic 510 and for quick release from the socket-connect portion 200. As illustrated in FIG. 6, the prosthetic-connect portion 300 may have a generally elongated shape with a prosthetic-connect head portion end 302 and a prosthetic-connect base portion end 304. A circumferential prosthetic-connect portion ridge 310 may extend from the outer surface of the prosthetic-connect portion 300 between the prosthetic-connect head portion end 302 and the prosthetic-connect base portion end 304.

In some embodiments, the prosthetic-connect portion head end 302 of the prosthetic-connect portion 300 may be configured to securely fasten to the prosthetic 510 through a fixed fastening mechanism known by those skilled in the art. In some embodiments, at least one fastener (not illustrated), such as a screw or bolt, for example and without limitation, may facilitate this fixed connection. Thus, both the prosthetic-connect portion 300 and the fixedly attached prosthetic 510 may together be detachably connected to the socket-connect portion 200 as the socket-connect portion 200 remains attached to the prosthetic socket 512.

Figure 7B:
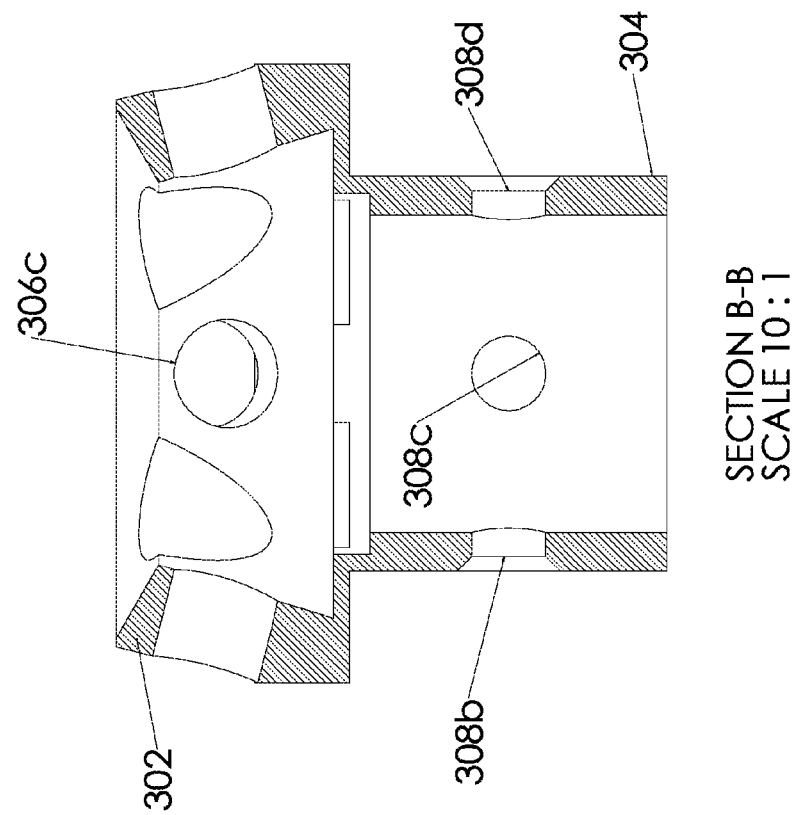
FIG. 7B illustrates a cross-sectional view, taken along section lines 7B-7B in FIG. 7A, of the exemplary prosthetic-connect portion of the quick-release prosthetic connector, detailing a head end having a plurality of prosthetic apertures and a base end having a plurality of spherical apertures, in accordance with an embodiment of the present invention.
Figure 7A:
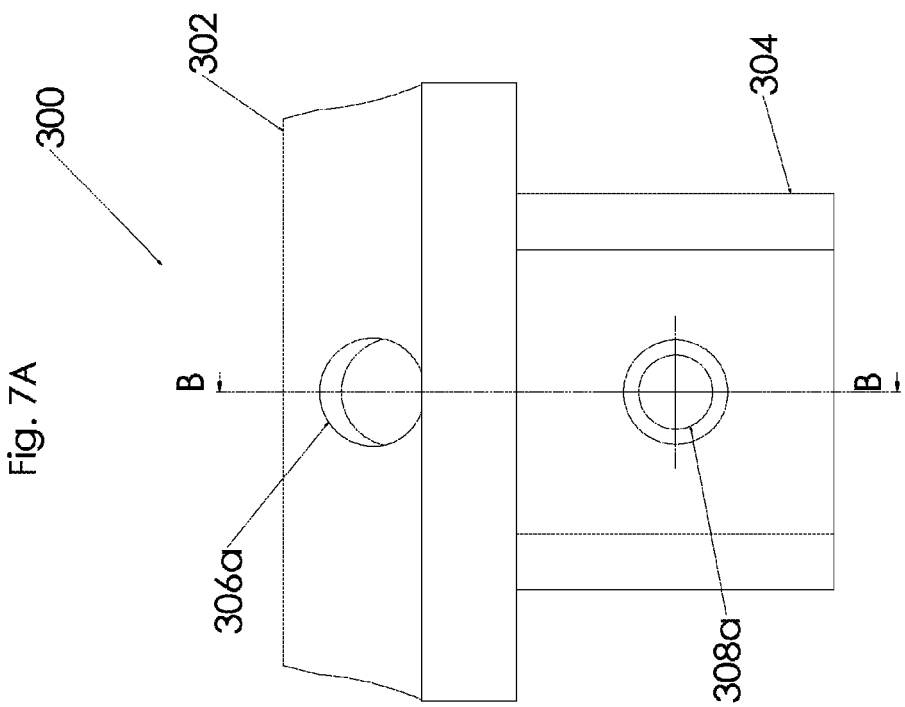
FIG. 7A illustrates a side view of an exemplary prosthetic-connect portion of the quick release prosthetic connector, in accordance with an embodiment of the present invention

As illustrated in FIGS. 7A-7C, in some embodiments, the prosthetic-connect base portion end 304 of the prosthetic-connect portion 300 may form a generally elongated rectangle having four walls. As illustrated in FIG. 7B, the prosthetic-connect base portion end 304 may include a plurality of typically spherical locking member engaging apertures 308a-d configured to selectively receive the typically spherical locking members 206a-d (FIG. 1) of the socket-connect portion 200 when the socking members 206a-d are deployed in the spring-biased position protruded from the respective locking member openings 212a-d. The locking member engaging apertures 308a-d in the prosthetic-connect portion 300 may be sized and dimensioned to form a snug fit with the respective companion locking members 206a-d. In some embodiments, the locking member engaging apertures 308a-d may include four spaced-apart locking member engaging apertures 308a-308d positioned in the respective walls of the prosthetic-connect base portion end 304 (FIG. 7D).

Figure 8:
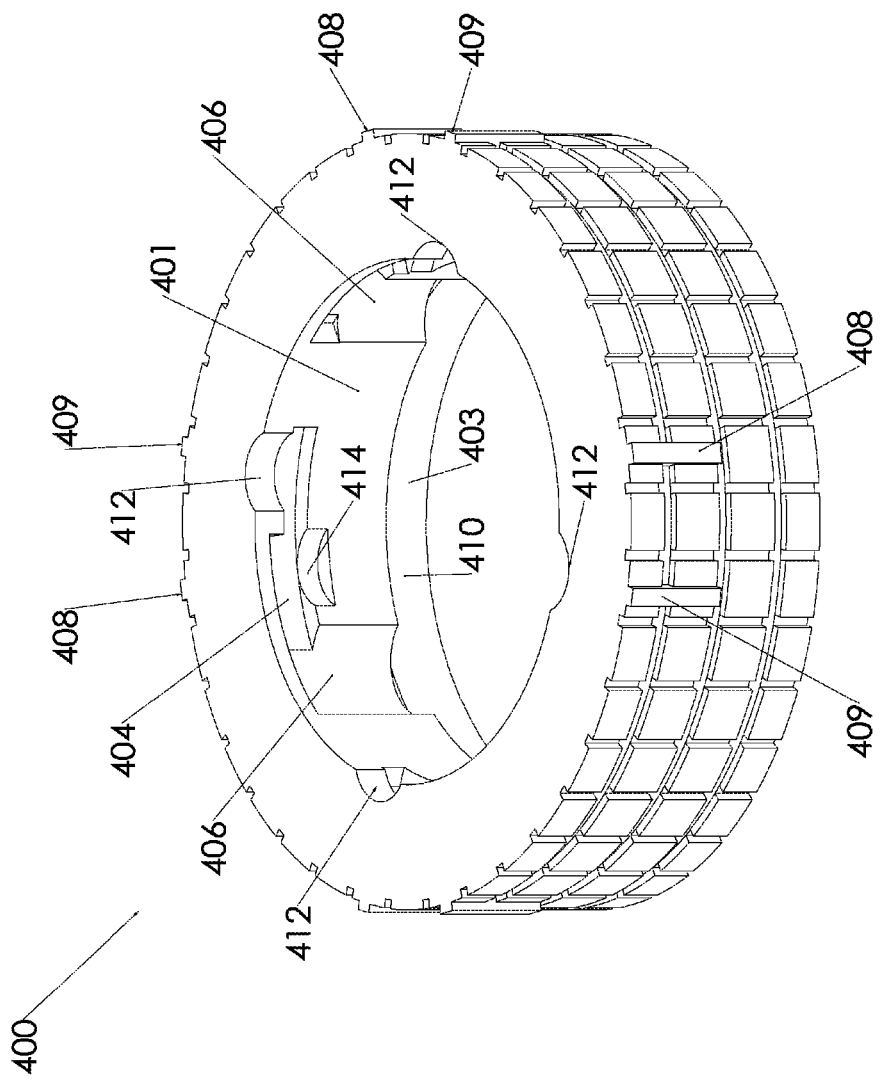
FIG. 8 illustrates a top angle perspective view of an exemplary lock portion of the quick-release prosthetic connector, in accordance with an embodiment of the present invention.

As illustrated in FIG. 8, a lock portion 400 may releasably lock the prosthetic-connect portion 300 to the socket-connect portion 200 of the connector 100. The lock portion 400 may have a generally annular shape that is sized and configured to generally encircle the socket-connect portion 200.

Figure 9D:
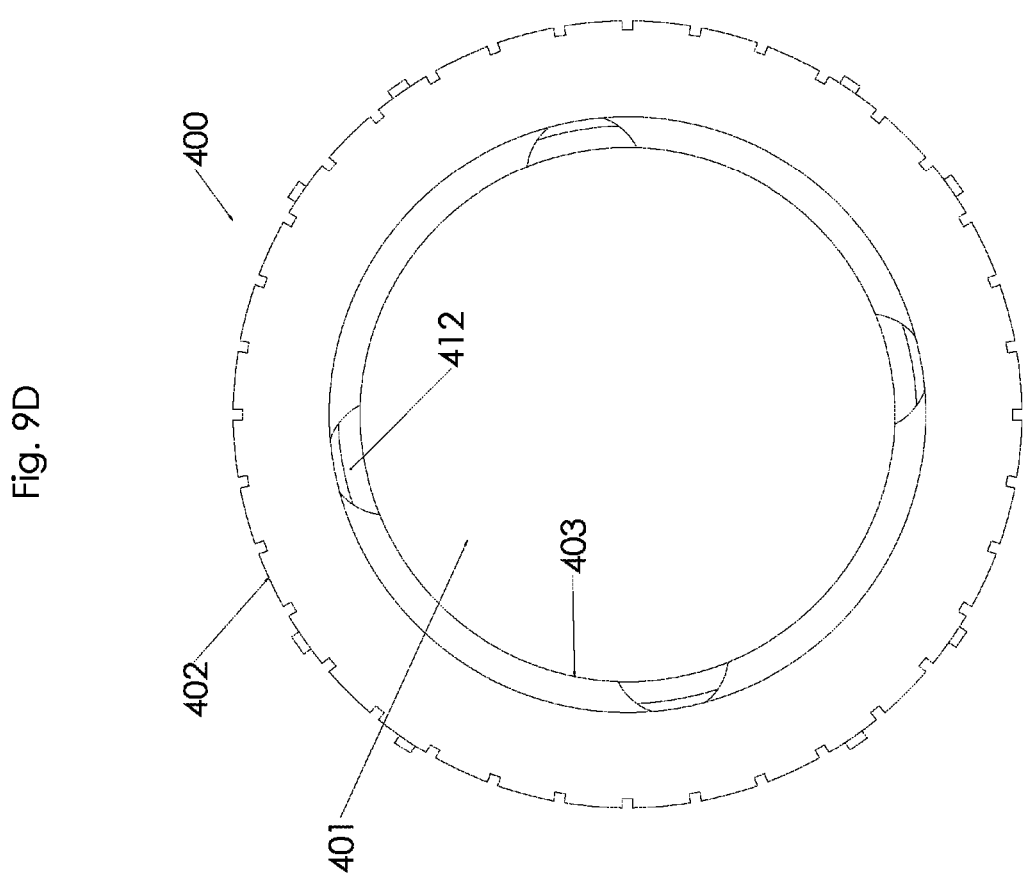
FIG. 9D illustrates a bottom view of the exemplary lock portion of the quick-release prosthetic connector, in accordance with an embodiment of the present invention.

As illustrated in FIGS. 9A-9D, the lock portion 400 may include an exterior lock portion surface 402 and an interior lock portion surface 403 which faces the lock portion opening 401. As illustrated in FIG. 9B, lock portion threads 410 may be provided in the interior lock portion surface 403. The lock portion threads 410 may threadably engage the exterior companion threaded socket-connect portion outer surface 208 (FIG. 4) of the socket-connect portion 200. In this manner, the lock portion 400 can rotate about and fasten to the socket-connect portion 200.

As illustrated in FIGS. 9B and 9C, the lock portion 400 may further include a plurality of lock portion depressions 406 provided in spaced-apart relationship to each other in the interior lock portion surface 403. The lock portion depressions 406 may be sized and configured to receive the respective locking members 206*a-d* of the socket-connect portion 200. Like the locking member engaging apertures 308*a-d*, the lock portion depressions 406 may be sized and dimensioned to form a snug fit with the respective companion locking members 206*a-d*. Thus, when deployed in the spring-biased, extended configuration, the locking members 206*a-d* can align or register with and extend through the respective locking member engaging apertures 308*a-d* of the prosthetic-connect portion 300 and seat in the respective lock portion depressions 406 in the lock portion 400. In some embodiments, the locking member engaging apertures 308*a-d* may include four spaced-apart locking member engaging apertures 308*a-d*.

As illustrated in FIGS. 1 and 9B, the lock portion 400 may further include at least one lock portion channel 404 in the interior lock portion surface 403. Each lock portion channel 404 may be generally elongated and may extend along a portion of the circumference of the interior lock portion surface 403. A release notch 412 may be provided in the interior lock portion surface 403 in communication with each lock portion channel 404. The release notch 412 may open to the lock portion end surface 405 of the lock portion 400. A lock notch 414 may be provided in the interior lock portion surface 403 in communication with each lock portion channel 404 and in offset relationship to the corresponding release notch 412.

Through simultaneous selective application of rotational and axial forces on the lock portion 400, the protrusions 210*a-d* on the broad socket-connect portion end 202 of the socket-connect portion 200 may traverse the respective lock portion channels 404 in the interior lock portion surface 403 of the lock portion 400 and engage the corresponding release notches 412 or the lock notches 414 to release or lock, respectively, the prosthetic-connect portion 300 with respect to the socket-connect portion 200. For example, the lock portion 400 may be simultaneously pressed toward the prosthetic-connect portion 300 and rotated about the socket-connect portion 200 in a first direction to slide the protrusions 210*a-d* in the respective lock portion channels 404 and into the respective lock notches 414. This action facilitates alignment of the lock portion depressions 406 in the interior lock portion surface 403 of the lock portion 400 with the respective locking member engaging apertures 308*a-d* in the prosthetic-connect portion 300 and the respective locking members 206*a-d* on the socket-connect portion 200. Consequently, the spring members 214*a-d* (FIG. 5B) extend the locking members 206*a-d* on the socket-connect portion 200 through the respective locking member engaging apertures 308*a-d* in the prosthetic-connect portion 300 and into snug engagement with the respective lock portion depressions 406 in the interior lock portion surface 403 of the lock portion 400, locking the prosthetic-connect portion 300 on the socket-connect portion 200. The lock portion 400 may subsequently be simultaneously pressed toward the socket-connect portion 200 and rotated in the opposite direction to disengage the protrusions 210*a-d* from the respective lock notches 414 and slide the protrusions 210*a-d* along the respective lock portion channels 404 into the respective release notches 412. This action misaligns the lock portion depressions 406 in the interior lock portion 403 of the lock portion 400 with respect to the respective locking member engaging apertures 308*a-d* in the prosthetic-connect portion 300 and the respective locking members 206*a-d* on the socket-connect portion 200, causing the interior lock portion surface 403 of the lock portion 400 to push and clear the locking members 206*a-d* from the respective locking member engaging apertures 3008*a-d* and into the respective locking member openings 212*a-d* (FIG. 5B) in the socket-connect portion 200, against the bias imparted by the respective spring members 214*a-d*, and unlocking the prosthetic-connect portion 300 on the socket-connect portion 200.

As set forth above, when aligned, the locking members 206*a-d* of the socket-connect portion 200 insert through the respective locking member engaging apertures 308*a-d* in the prosthetic-connect portion 300 and seat in the respective lock portion depressions 406 in the interior lock portion surface 403 of the lock portion 400 as the spring members 214*a-d* (FIG. 5B) bias the locking members 206*a-d* from the respective locking member openings 212*a-d*. This extended configuration of the locking members 206*a-d* facilitates locked attachment of the prosthetic-connect portion 300 to the socket-connect portion 200. When misaligned, the locking members 206*a-d* of the socket-connect portion 200 disengage from the respective lock portion depressions 406 and locking member engaging apertures 308*a-d*. This disengagement facilitates release of the prosthetic-connect portion 300 from the socket-connect portion 200.

FIGS. 1 and 2 illustrate a typical manner in which the unique in-and-out movement of the locking members 206*a-d* serves to lock and release the prosthetic-connect portion 300 with the socket-connect portion 200. The release configuration, in which the prosthetic 510 is quick-released from the prosthetic socket 512, is achieved by alignment of the at least one release notch 412 on the lock portion 400 with the at least one protrusion 210*a-d* on the socket-connect portion 200. This alignment may serve to unseat or disengage the locking members 206*a-d* from the respective lock portion depressions 406 in the lock portion 400, against the spring bias applied by the spring members 214*a-d*, and facilitate release of the prosthetic-connect portion 300 from the socket-connect portion 200.

Conversely, the locked configuration, in which the prosthetic 510 is securely attached to the prosthetic socket 512, may be achieved by selective alignment of the at least one lock notch 414 in the lock portion 400 with the at least one protrusion 210*a-d* on the socket-connect portion 200 as the at least one protrusion 210*a-d* traverses the at least one lock portion channel 404 from the at least one release notch 412 to the at least one lock notch 414, responsive to rotation of and typically application of axial pressure to the lock portion 400. Alignment of the at least one protrusion 210*a-d* with the at least one lock notch 414 facilitates extension of the locking members 206*a-d* through the respective locking member engaging apertures 308*a-d* of the prosthetic-connect portion 300 and into the respective lock portion depressions 406 of the lock portion 400, responsive to the biasing action of the respective spring members 214a-d (FIG. 5B). This extended configuration of the locking members 206a-d locks the prosthetic-connect portion 300 with respect to the socket-connect portion 200.

As discussed above, the locking and unlocking movement of the locking members 206a-d may correspond to alignment or registration of the protrusions 210a-d with the corresponding release notches 412 and lock notches 414, respectively, through rotational and axial forces applied to the lock portion 400. In one exemplary use, the lock portion 400 may be pressed toward the prosthetic-connect portion 300 and rotated in a first direction to align the protrusions 210a-d with the respective lock notches 414 and extend the locking members 206a-d through the respective locking member engaging apertures 308a-d in the prosthetic-connect portion 300 and into the respective lock portion depressions 406 in the lock portion 400. This action locks the prosthetic-connect portion 300 on the socket-connect portion 200. Conversely, the lock portion 400 may be subsequently pressed toward the socket-connect portion 200 and rotated in a second direction to disengage the protrusions 210a-d from the respective lock notches 414, slide the protrusions 210a-d along the respective lock portion channels 404 and insert the protrusions 210a-d into the respective release notches 412. Accordingly, the interior lock portion surface 403 of the lock portion 400 pushes the locking members 206a-d into the respective locking member openings 212a-d against the spring bias of the respective spring members 214a-d in the socket-connect portion 200 such that the locking members 206a-d clear the locking member engaging apertures 308a-d in the prosthetic-connect portion 300. This action unlocks the prosthetic-connect portion 300 on the socket-connect portion 200 and enables release of the prosthetic-connect portion 300 and attached prosthetic 510 from the socket-connect portion 200.

As illustrated in FIG. 9C, in some embodiments, at least one pair of a lock portion slit 408 and a release portion slit 409 may be provided in the lock portion end surface 405 and/or the exterior lock portion surface 402 of the lock portion 400. Each lock portion slit 408 may be disposed adjacent to and in alignment with a corresponding lock notch 414 in the interior lock portion surface 403 of the lock portion 400. The lock portion slit 408 may indicate alignment or registration of the at least one protrusion 210a-d on the socket-connect portion 200 with the corresponding lock notch 414 in the interior lock portion surface 403 of the lock portion 400 when the prosthetic-connect portion 300 is locked on the socket-connect portion 200. Each release portion slit 409 may be disposed adjacent to and in alignment with a corresponding release notch 412 in the interior lock portion surface 403 of the lock portion 400. Accordingly, the release portion slit 409 may indicate alignment or registration of the at least one protrusion 210a-d on the socket-connect portion 200 with the corresponding release notch 412 in the interior lock portion surface 403 of the lock portion 400 when the prosthetic-connect portion 300 is unlocked on the socket-connect portion 200. In some embodiments, the lock portion slit 408 may be labeled "Lock", whereas the release portion slit 409 may be labeled "Release".

These and other advantages of the invention will be further understood and appreciated by those skilled in the art by reference to the following written specification, claims and appended drawings.

Because many modifications, variations, and changes in detail can be made to the described preferred embodiments of the invention, it is intended that all matters in the foregoing description and shown in the accompanying drawings be interpreted as illustrative and not in a limiting sense. Thus, the scope of the invention should be determined by the appended claims and their legal equivalence.

What is claimed is:

1. A quick release prosthetic connector for detachably joining a prosthetic to a prosthetic socket, the connector comprising:
   a socket-connect portion configured for connection to the prosthetic socket;
   a plurality of locking members carried by the socket-connect portion, the plurality of locking members positional between a release position and a locking position, the plurality of locking members normally biased in the locking position;
   a prosthetic-connect portion configured for connection to the prosthetic;
   a plurality of locking member engaging apertures in the prosthetic-connect portion, the plurality of locking member engaging apertures configured to selectively receive the plurality of locking members, respectively, of the socket-connect portion in the locking position of the plurality of locking members;
   a lock portion carried by the socket-connect portion, the lock portion configured to selectively lock and release the prosthetic-connect portion with respect to the socket-connect portion;
   a plurality of lock portion depressions in the lock portion, the plurality of lock portion depressions configured to selectively receive the plurality of locking members, respectively, of the socket-connect portion in the locking position of the plurality of locking members;
   a threaded socket-connect portion outer surface on the socket-connect portion, the threaded socket-connect portion outer surface configured to threadably engage the prosthetic socket, wherein the socket-connect portion comprises a broad socket-connect portion end and a narrow socket-connect portion end, and wherein the threaded socket-connect portion outer surface is between the broad socket-connect portion end and the narrow socket-connect portion end;
   whereby the plurality of locking members are deployed in the locking position and extend through the plurality of locking member engaging apertures, respectively, in the prosthetic-connect portion and seat in the respective lock portion depressions in the lock portion responsive to rotation of the lock portion in a first direction; and
   whereby the plurality of locking members are deployed in the unlocking position and disengage the plurality of locking member engaging apertures, respectively, in the prosthetic-connect portion and the respective lock portion depressions in the lock portion responsive to rotation of the lock portion in a second direction.

2. The quick release prosthetic connector of claim 1 wherein the socket-connect portion comprises a comprises a prosthetic-connect head portion end and a prosthetic-connect base portion end, and wherein the plurality of locking member engaging apertures extend through the prosthetic-connect base portion end.

3. The quick release prosthetic connector of claim 1 wherein the lock portion comprises a lock portion opening, an interior lock portion surface facing the lock portion opening, an exterior lock portion surface opposite the interior lock portion surface and a lock portion end surface extending between the interior lock portion surface and the exterior lock portion surface, and wherein the plurality of lock portion depressions is in the interior lock portion surface.

4. The quick release prosthetic connector of claim 1 further comprising a plurality of spaced-apart locking member openings in the socket-connect portion, and wherein the plurality of locking members are disposed in the plurality of locking member openings, respectively.

5. The quick release prosthetic connector of claim 1 wherein the plurality of locking members comprises a plurality of metal balls.

6. The quick release prosthetic connector of claim 1 further comprising a plurality of prosthetic apertures in the prosthetic-connect portion, the plurality of prosthetic apertures configured to facilitate connection of a prosthetic-connect head portion end to the prosthetic-connect portion.

7. A quick release prosthetic connector for detachably joining a prosthetic to a prosthetic socket, the connector comprising:
  a socket-connect portion configured for connection to the prosthetic socket;
  a plurality of locking members carried by the socket-connect portion, the plurality of locking members positional between a release position and a locking position, the plurality of locking members normally biased in the locking position;
  at least one protrusion carried by the socket-connect portion;
  a prosthetic-connect portion configured for connection to the prosthetic;
  a plurality of locking member engaging apertures in the prosthetic-connect portion, the plurality of locking member engaging apertures configured to selectively receive the plurality of locking members, respectively, of the socket-connect portion in the locking position of the plurality of locking members;
  a lock portion carried by the socket-connect portion, the lock portion configured to selectively lock and release the prosthetic-connect portion with respect to the socket-connect portion;
  a plurality of lock portion depressions in the lock portion, the plurality of lock portion depressions configured to selectively receive the plurality of locking members, respectively, of the socket-connect portion in the locking position of the plurality of locking members;
  at least one lock portion channel in the lock portion, the at least one lock portion channel receives the at least one protrusion;
  at least one lock notch in the lock portion, the at least one lock notch communicating with the at least one lock portion channel, the at least one lock notch receives the at least one protrusion in the locking position of the plurality of locking members;
  at least one release notch in the lock portion, the at least one release notch communicating with the at least one lock portion channel in offset relationship to the at least one lock notch, the at least one lock notch receives the at least one protrusion in the locking position of the plurality of locking members;
  whereby the plurality of locking members are deployed in the locking position and extend through the plurality of locking member engaging apertures, respectively, in the prosthetic-connect portion and seat in the respective lock portion depressions in the lock portion responsive to rotation of the lock portion in a first direction;
  whereby the plurality of locking members are deployed in the unlocking position and disengage the plurality of locking member engaging apertures, respectively, in the prosthetic-connect portion and the respective lock portion depressions in the lock portion responsive to rotation of the lock portion in a second direction;
  whereby alignment of the at least one protrusion on the socket-connect portion with the at least one lock notch of the lock portion facilitates extension of the plurality of locking members through the plurality of locking member engaging apertures in the prosthetic-connect portion and into the plurality of lock portion depressions in the lock portion, locking the prosthetic-connect portion with respect to the socket-connect portion; and
  whereby alignment of the at least one protrusion with the at least one release notch facilitates disengagement of the plurality of locking members from the plurality of locking member engaging apertures in the prosthetic-connect portion and from the plurality of lock portion depressions in the lock portion, facilitating release of the prosthetic-connect portion from the socket-connect portion.

8. The quick release prosthetic connector of claim 7 wherein the socket-connect portion comprises a comprises a prosthetic-connect head portion end and a prosthetic-connect base portion end, and wherein the plurality of locking member engaging apertures extend through the prosthetic-connect base portion end.

9. The quick release prosthetic connector of claim 7 further comprising a threaded socket-connect portion outer surface on the socket-connect portion, the threaded socket-connect portion outer surface configured to threadably engage the prosthetic socket.

10. The quick release prosthetic connector of claim 9 wherein the socket-connect portion comprises a broad socket-connect portion end and a narrow socket-connect portion end, and wherein the threaded socket-connect portion outer surface is between the broad socket-connect portion end and the narrow socket-connect portion end.

11. The quick release prosthetic connector of claim 7 wherein the lock portion comprises a lock portion opening, an interior lock portion surface facing the lock portion opening, an exterior lock portion surface opposite the interior lock portion surface and a lock portion end surface extending between the interior lock portion surface and the exterior lock portion surface, and wherein the plurality of lock portion depressions is in the interior lock portion surface.

12. The quick release prosthetic connector of claim 7 further comprising a plurality of locking member openings in the socket-connect portion, and wherein the plurality of locking members are disposed in the plurality of locking member openings, respectively.

13. The quick release prosthetic connector of claim 7 wherein the plurality of locking members comprises a plurality of metal balls.

14. The quick release prosthetic connector of claim 7 further comprising a plurality of prosthetic apertures in the prosthetic-connect portion, the plurality of prosthetic apertures configured to facilitate connection of the prosthetic to the prosthetic-connect portion.

15. A quick release prosthetic connector for detachably joining a prosthetic to a prosthetic socket, the connector comprising:
  a socket-connect portion configured for connection to the prosthetic socket, the socket-connect portion having a broad socket-connect portion end and a narrow socket-connect portion end;

a plurality of locking member openings in the broad socket-connect portion end of the socket-connect portion;

a plurality of locking members in the plurality of locking member openings, respectively, of the socket-connect portion, the plurality of locking members positional between a release position and a locking position;

a plurality of spring members in the plurality of locking member openings, respectively, the plurality of spring members normally biasing the plurality of locking members, respectively, in the locking position;

at least one protrusion carried by the broad socket-connect portion end of the socket-connect portion;

a prosthetic-connect portion configured for connection to the prosthetic, the prosthetic-connect portion having a prosthetic-connect head portion end and a prosthetic-connect base portion end, the prosthetic-connect base portion end inserted in the broad socket-connect portion end of the socket connect portion;

a plurality of locking member engaging apertures in the prosthetic-connect base portion end of the prosthetic-connect portion, the plurality of locking member engaging apertures configured to selectively receive the plurality of locking members, respectively, of the socket-connect portion in the locking position of the plurality of locking members;

a lock portion receiving the broad socket-connect portion end of the socket-connect portion, the lock portion configured to selectively lock and release the prosthetic-connect portion with respect to the socket-connect portion;

a plurality of lock portion depressions in the lock portion, the plurality of lock portion depressions configured to selectively receive the plurality of locking members, respectively, of the socket-connect portion in the locking position of the plurality of locking members;

at least one lock portion channel in the lock portion, the at least one lock portion channel receives the at least one protrusion on the broad socket-connect portion end of the socket-connect portion;

at least one lock notch in the lock portion, the at least one lock notch communicating with the at least one lock portion channel, the at least one lock notch receives the at least one protrusion in the locking position of the plurality of locking members;

at least one release notch in the lock portion, the at least one release notch communicating with the at least one lock portion channel in offset relationship to the at least one lock notch, the at least one lock notch receives the at least one protrusion in the release position of the plurality of locking members;

whereby the plurality of locking members are deployed in the locking position and extend through the plurality of locking member engaging apertures, respectively, in the prosthetic-connect portion and seat in the respective lock portion depressions in the lock portion responsive to rotation of the lock portion in a first direction;

whereby the plurality of locking members are deployed in the unlocking position and disengage the respective lock portion depressions in the lock portion and the plurality of locking member engaging apertures, respectively, in the prosthetic-connect portion responsive to rotation of the lock portion in a second direction;

whereby alignment of the at least one protrusion on the socket-connect portion with the at least one lock notch of the lock portion facilitates extension of the plurality of locking members through the plurality of locking member engaging apertures in the prosthetic-connect portion and into the plurality of lock portion depressions in the lock portion, locking the prosthetic-connect portion with respect to the socket-connect portion; and whereby alignment of the at least one protrusion with the at least one release notch facilitates disengagement of the plurality of locking members from the plurality of lock portion depressions, respectively, in the lock portion and from the plurality of locking member engaging apertures, respectively, in the prosthetic-connect portion, facilitating release of the prosthetic-connect portion from the socket-connect portion.

16. The quick release prosthetic connector of claim 15 wherein the lock portion comprises a lock portion opening, an interior lock portion surface facing the lock portion opening, an exterior lock portion surface spaced-apart from the interior lock portion surface and a lock portion end surface extending between the interior lock portion surface and the exterior lock portion surface, and wherein the plurality of lock portion depressions, the at least one lock portion channel, the at least one lock notch and the at least one release notch are provided in the interior lock portion surface.

17. The quick release prosthetic connector of claim 16 further comprising at least one lock portion slit in at least one of the exterior lock portion surface and the lock portion end surface of the lock portion, the at least one lock portion slit disposed adjacently to and in alignment with the at least one lock notch, the at least one lock portion slit configured to indicate alignment of the at least one protrusion on the socket-connect portion with the at least one lock notch in the lock portion.

18. The quick release prosthetic connector of claim 17 further comprising at least one release portion slit in at least one of the exterior lock portion surface and the lock portion end surface of the lock portion, the at least one release portion slit disposed adjacently to and in alignment with the at least one release notch, the at least one release portion slit configured to indicate alignment of the at least one protrusion on the socket-connect portion with the at least one release notch in the lock portion.

* * * * *